United States Patent
Elowe et al.

(10) Patent No.: US 9,382,192 B2
(45) Date of Patent: Jul. 5, 2016

(54) NONIONIC SURFACTANT COMPOSITIONS

(71) Applicant: DOW GLOBAL TECHNOLOGIES LLC, Midland, MI (US)

(72) Inventors: Paul R. Elowe, Midland, MI (US); Arkady L. Krasovskiy, Midland, MI (US); Irina V. Graf, Midland, MI (US); Lin Wang, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 89 days.

(21) Appl. No.: 14/378,848

(22) PCT Filed: Feb. 14, 2013

(86) PCT No.: PCT/US2013/026088
§ 371 (c)(1),
(2) Date: Aug. 14, 2014

(87) PCT Pub. No.: WO2013/123153
PCT Pub. Date: Aug. 22, 2013

(65) Prior Publication Data
US 2016/0016886 A1    Jan. 21, 2016

Related U.S. Application Data

(60) Provisional application No. 61/598,469, filed on Feb. 14, 2012.

(51) Int. Cl.
C07C 217/08 (2006.01)
C07C 213/08 (2006.01)
C07C 209/28 (2006.01)

(52) U.S. Cl.
CPC ............. *C07C 213/08* (2013.01); *C07C 209/28* (2013.01); *C07C 217/08* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 2,627,491 A | 2/1953 | Szabo et al. | |
| 3,235,627 A | 2/1966 | Mansfield | |
| 3,244,750 A * | 4/1966 | Humber | 564/123 |
| 4,174,406 A | 11/1979 | Bordenca | |
| 5,250,230 A | 10/1993 | Steele et al. | |
| 6,143,419 A | 11/2000 | Hanada et al. | |
| 2003/0162676 A1 | 8/2003 | Serve et al. | |

FOREIGN PATENT DOCUMENTS

| | | |
|---|---|---|
| EP | 0930346 | 7/1999 |
| EP | 1749566 | 2/2007 |

OTHER PUBLICATIONS

Pastor et al., "Chiral Cooperativity: The Effect of Distant Chiral Centers in Ferrocenylamine Ligands Upon Enanthioselectivity in Gold(I)-Catalyzed Aldol Reaction" Helvetica Chimica Acta, vol. 74, No. 5, pp. 905-933 (1991).
Kirillov et al., "Chiral Fluorous Dialkoxy-Diamino Zirconium Complexes: Synthesis and Use in Stereospecific Polymerization of 1-Hexene" Chem Eur. J, vol. 13, pp. 923-935 (2007).
Mattson et al., "An improved method for reductive alkylation of amines using titanium(Iv) isopropoxide and sodium cyanoborohydride" J. Org. Chem., vol. 55, No. 8, pp. 2552-2554 (1990).
Abdel-Magid et al., "Reductive Amination of Aldehydes and Ketones with Sodium Triacetoxyborohydride" J. Org. Chem. vol. 61, pp. 3849-3862 (1996).
Emerson, "The Preparation of Amines by Reductive Alkylation", Organic Reactions, vol. 4, pp. 174-255, 1948.
Baxter et al., "Reductive Aminations of Carbonyl Compounds with Borohydride and Borane Reducing Agents", Organic Reactions, vol. 59, pp. 39-54, 2002.
Abdel-Magid et al. "A Review on the Use of Sodium Triacetoxyborohydride in the Reductive Amination of Ketones and Aldehydes" Org. Process Res. & Dev. vol. 10, pp. 971-1031, 2006.
Zana et al., "Gemini Surfactants: Synthesis, Interfacial and Solution-Phase Behavior, and Applications" Journal of Colloid and Interface Science, 272, p. 502, 2004.
Rosen, M. J. Surfactants and Interfacial Phenomena, $3^{rd}$ ed.; John Wiley & Sons, Inc.; Hoboken, New Jersey, pp. 243-277, 2004.

* cited by examiner

*Primary Examiner* — Fereydoun G Sajjadi
*Assistant Examiner* — Jennifer C Sawyer
(74) *Attorney, Agent, or Firm* — Brooks, Cameron & Huebsch, PLLC

(57) ABSTRACT

The present invention provides nonionic surfactants, compositions incorporating these surfactants, and related methods of making and using such surfactants and compositions. The nonionic surfactants demonstrate excellent equilibrium and dynamic surface tension properties as well as excellent wetting properties. Further, representative embodiments of the surfactants have shown low foaming characteristics, indicating that the surfactants would be suitable in applications where resistance to foaming is desired. The surfactants can be used singly or in combination with other nonionic and/or ionic surfactants as desired. As an over view, the nonionic surfactants of the present invention have a structure in which the surfactant backbone includes one or more amine moieties. At least one, preferably two or more branched, cyclic, fused cyclic, and/or spyro hydrophobic moieties are pendant from at least one of the amine moieties. Additionally, at least one, preferably two or more hydrophilic moieties, preferably alkylene oxide (i.e., polyether) chains also are pendant from at least one of the amine moieties.

3 Claims, No Drawings

NONIONIC SURFACTANT COMPOSITIONS

PRIORITY

This application claims priority to International Application No. PCT/US2013/026088, filed on Feb. 14, 2013, which in turn claims priority under 35 U.S.C. §119(e) to U.S. provisional application No. 61/598,469, titled "NONIONIC SURFACTANT COMPOSITIONS," filed Feb. 14, 2012, wherein the disclosures of these applications are incorporated herein by reference in their respective entireties for all purposes.

FIELD OF THE INVENTION

The present invention relates to nonionic surfactants. More particularly, the present invention relates to nonionic surfactants comprising one or more amine moieties, one or more branched hydrophobic chains pendant from the amine moieties, and one or more hydrophilic alkylene oxide chains pendant from the amine moieties.

BACKGROUND OF THE INVENTION

The ability to reduce the surface tension of liquid compositions, particularly aqueous compositions, is of great importance in a wide variety of compositions including solutions, dispersions, gels, emulsions, latex compositions, and the like. Such compositions are used in a wide range of applications including paints and other coatings, stains and other coloring agents, ink compositions, oil and gas recovery compositions, steam assisted gravity drainage compositions, chemical flooding compositions, cosmetics, foods, nutriceuticals, health care products, cleaning products, etching compositions, agrochemicals, or the like.

It is well known in the art that so-called Gemini surfactants, which are surfactants with multiple hydrophobic tails and multiple hydrophilic heads, or Gemini-like surfactants exhibit superior properties compared to those of analogous conventional surfactants. See, e.g., *Gemini Surfactants: Synthesis, Interfacial and Solution-Phase Behavior, and Applications*, Vol. 117, Zana, R.; Xia, J., Eds.; Marcel Dekker: New York, 2004. Furthermore, it is also well known in the art that increasing branching in a hydrophobic tail significantly improves wetting properties of a surfactant. See, e.g., Rosen, M. J. *Surfactants and Interfacial Phenomena*, 3$^{rd}$ ed.; John Wiley & Sons, Inc.; Hoboken, N. J., 2004; pp. 243-277.

Important surfactant performance characteristics include equilibrium surface tension properties, dynamic surface tension properties, wetting properties, foaming properties, and the like. Equilibrium surface tension is important when a system is at rest. Dynamic surface tension is a fundamental property which measures the ability of a surfactant to perform under high speed application conditions. Many nonionic surfactants may have acceptable equilibrium surface tension properties, but demonstrate poor dynamic surface tension properties. Many nonionic surfactants also tend to be foamy and make compositions too susceptible to foaming, which can be undesirable in many applications. The importance of improving equilibrium, dynamic, wetting and foaming performance is well-appreciated in the art.

Accordingly, there is a strong demand for nonionic surfactants that provide not only strong equilibrium surface tension properties but also strong dynamic surface tension properties and strong wetting properties with a reduced tendency to cause foaming.

SUMMARY OF THE INVENTION

The present invention provides nonionic surfactants, compositions incorporating these surfactants, and related methods of making and using such surfactants and compositions. The nonionic surfactants demonstrate excellent equilibrium and dynamic surface tension properties as well as excellent wetting properties. Further, representative embodiments of the surfactants have shown low foaming characteristics, indicating that the surfactants would be suitable in applications where resistance to foaming is desired. The surfactants can be used singly or in combination with other nonionic and/or ionic surfactants as desired.

As an overview, the nonionic surfactants of the present invention have a structure in which the surfactant backbone includes one or more amine moieties. At least one, preferably two or more branched, cyclic, fused cyclic, and/or spyro hydrophobic moieties are pendant from at least one of the amine moieties. Additionally, at least one, preferably two or more hydrophilic moieties, preferably alkylene oxide (i.e., polyether) chains also are pendant from at least one of the amine moieties.

In one aspect, the present invention relates to a method of making a nonionic surfactant, comprising the steps of:
  a) providing an adduct comprising at least one secondary amine moiety and at least two branched, cyclic, fused cyclic, and/or spyro hydrophobic moieties; and
  b) N-functionalizing at least a portion of the secondary amine moieties of the adduct under conditions effective to convert at least a portion of the secondary amine moieties to tertiary amine moieties having pendant, hydrophilic, N-ether functionality.

In another aspect, the present invention relates to a nonionic surfactant of the formula

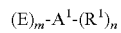

wherein:
  $A^1$ is an (n+m) valent moiety comprising at least one tertiary amine moiety and optionally one or more secondary amine moieties;
  each $R^1$ independently is a branched, cyclic, fused cyclic, and/or spyro hydrophobic moiety;
  each E independently is H or an N-functional, monovalent moiety of the formula

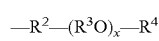

with the proviso that at least one E is not H, wherein each $R^2$ independently is a single bond or a divalent linking group; each $R^3$ is independently an alkylene moiety containing from 1 to 5 carbon atoms (e.g., each alkylene oxide chain independently may contain one or more different kinds of alkylene oxide units used in combination; and each alkylene oxide chain may be the same or different than other such chains included in the molecule); each x independently is 1 to 100; and each $R^4$ independently is H or a monovalent moiety comprising from 1 to 8 carbon atoms;
  n is 2 to 6; and
  m is 1 to 6.

DETAILED DESCRIPTION OF PRESENTLY PREFERRED EMBODIMENTS

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention. All patents, pending patent applications, published patent applications, and technical articles cited herein are incorporated herein by reference in their respective entireties for all Purposes.

The present invention relates to nonionic surfactants of the formula

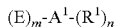

wherein:
$A^1$ is an (n+m) valent moiety comprising at least one, more preferably at least two tertiary amine moieties, and optionally one or more secondary amine moieties;
each $R^1$ independently is a branched, cyclic, fused cyclic, and/or spyro hydrophobic moiety;
each E independently is H or an N-functional, monovalent moiety of the formula

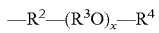

with the proviso that at least one E is not H and more preferably at least two E are not H, wherein each $R^2$ independently is a single bond or a divalent linking group; each $R^3$ is independently a linear or branched alkylene moiety containing from 1 to 5 carbon atoms (e.g., each alkylene oxide chain independently may contain one or more different kinds of alkylene oxide units used in combination; and each alkylene oxide chain may be the same or different than other such chains included in the molecule); each x independently has an average value of 1 to 100; and each $R^4$ independently is H or a monovalent moiety comprising from 1 to 8 carbon atoms;
n is 2 to 6, preferably 2 to 3, more preferably 2; and
m is 1 to 6, preferably 1 to 3, more preferably 1 to 2.

Preferably, each of n and m independently are 2 to 4. In some embodiments, n=m. Even more preferably, each of n and m are 2.

As used herein, a hydrophobic moiety refers to a moiety in which the ratio of carbon atoms to hetero atoms (such as O, P, S or the like) in the moiety is 5:1 or greater, preferably 8:1 or greater, more preferably 12:1 or greater. Even more preferably, a hydrophobic moiety is a hydrocarbyl or hydrocarbylene moiety that (1) contains at least 5 carbon atoms, (2) contains only C and H atoms, (3) is free of hetero atoms such as O, P, and S or the like; and (4) optionally is branched and/or has a ring, spyro, and/or fused ring structure.

As used herein, the terminology "N-functional" means that a moiety is pendant from a nitrogen atom.

In exemplary embodiments, each $R^3$ moiety independently may be ethylene, propylene, isopropylene, butylene, isobutylene, or combinations thereof. Preferably, each $R^3$ moiety is ethylene, propylene, butylene or combinations thereof. More preferably, $R^3$ is ethylene.

As shown by the general formula, the value for x may be selected over a wide range. In preferred embodiments, each x independently has an average value of 1 to 20, preferably 1 to 10, more preferably 1 to 4. When a surfactant includes 2 or more E moieties, it is desirable that the values for x for all the E moieties are generally matched on average. For instance, if a surfactant embodiment has two E moieties and one of the E moieties has an average x=4, then it is desirable that the other E has an average x=3 to 5, more preferably x=3.5 to 4.5, more preferably x=4.

A first, preferred class of surfactants of the present invention may be represented by the general formula

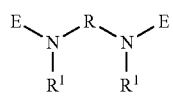

wherein E and $R^1$ are as defined above, and R is a divalent linking group. One exemplary first group of surfactants according to this first class includes surfactants according to the following formula:

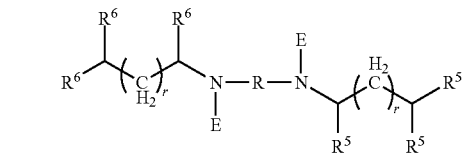

wherein E and R are as defined above, wherein R preferably is a divalent moiety that may be linear, branched, cyclic, fused cyclic, spyro, saturated or unsaturated, aliphatic or aromatic, substituted or unsubstituted, and more preferably is a hydrocarbylene moiety of 1 to 20 carbon atoms; each $R^5$ and each $R^6$ independently is H, a monovalent hydrocarbyl moiety comprising 1 to 20 carbon atoms, or a co-member of a hydrocarbylene ring structure with at least one other $R^5$ or $R^6$, with the proviso that at least one $R^5$ and at least one $R^6$ is not H; and each r independently is 0 to 20.

More preferably, the first group of surfactants is exemplified by surfactants having the formula

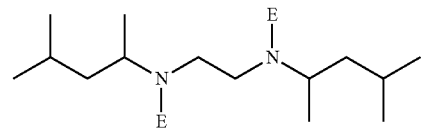

and/or of the formula

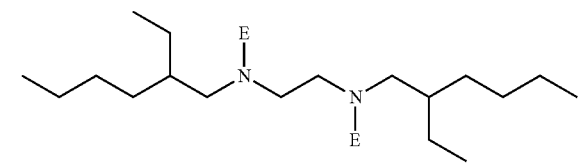

wherein each E independently is as defined above, and in the formula for E, $R^2$ is a single bond and $R^3$ independently is selected from one or more of ethylene, propylene, butylene or combinations thereof.

A particularly preferred embodiment of a surfactant of the type shown in Paragraph 19 has the formula

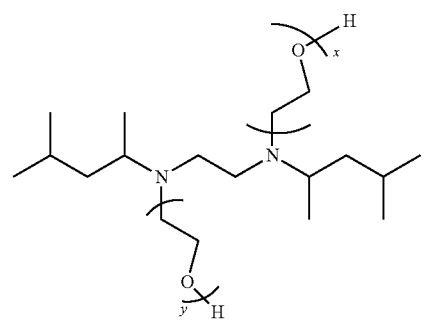

wherein when dynamic properties are to be favored, each of x and y is on average independently 0 to 6, preferably independently 0 to 4, with the proviso that x+y on average is 1 to 12, preferably 1 to 8. Comparable versions of the surfactants described in paragraphs 20 and 21 independently would have similar structures for each E to favor dynamic properties. More generally, to favor dynamic properties for the surfactants of the first class of surfactants of Paragraph 16 above or the second class of surfactants of Paragraph 29 below, each E independently generally includes on average from 0 to 6, preferably from 0 to 4 ethylene oxide units, with the proviso that the total number of ethylene oxide units in all the E moieties of the surfactant on average is 1 to 12, preferably 1 to 8.

In other embodiments of the first class of surfactants of Paragraph 16 above or the second class of surfactants of Paragraph 29 below more suitable for oil and gas applications or the like, each E independently includes a combination comprising ethylene oxide (EO) and optionally and preferably propylene oxide (PO) moieties, wherein the molar ratio of EO to PO moieties (when PO moieties are present) in each E independently is in the range from 100:1 to 1:100, desirably 20:1 to 1:20; the average number of EO units in each E independently is in the range from 1 to 100, preferably 1 to 50; and the average number of PO units in each E is in the range from 0 to 100, preferably 0 to 20; and the total number of EO and PO units in the E moieties is in the range from 1 to 200, preferably 1 to 100, more preferably 1 to 70.

An exemplary second group of surfactants according to the first class of surfactants includes surfactants according to the following formula:

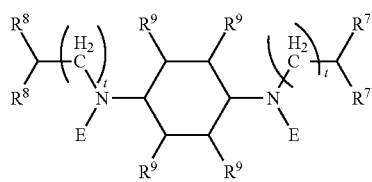

wherein each $R^7$ and each $R^8$ independently is a monovalent moiety comprising 1 to 20 carbon atoms or is a co-member of a ring structure; each $R^9$ independently is H, a monovalent moiety comprising 1 to 20 carbon atoms, or a co-member of a ring structure; and each t independently is 1 to 20, preferably 1 to 6. A particularly preferred nonionic surfactant of this type has the formula

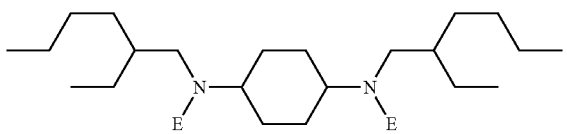

An exemplary third group of surfactants according to the first class of surfactants includes surfactants according to the following formula:

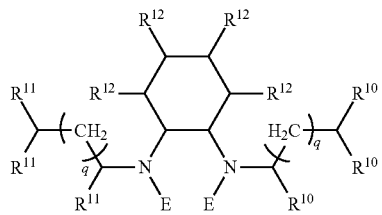

wherein each $R^{10}$ and each $R^{11}$ independently is a monovalent moiety comprising 1 to 20 carbon atoms or is a co-member of a ring structure; each $R^{12}$ independently is H, a monovalent moiety comprising 1 to 20 carbon atoms, or a co-member of a ring structure; and each q independently is 1 to 20. A particularly preferred nonionic surfactant of this type has the formula

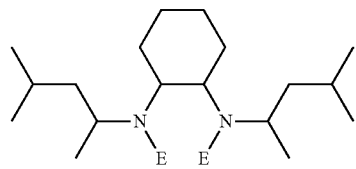

A second, representative class of surfactants of the present invention may be represented by the general formula

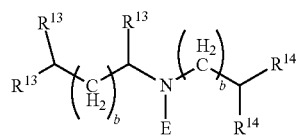

wherein each $R^{13}$ and each $R^{14}$ independently is a monovalent moiety comprising 1 to 20 carbon atoms or is a co-member of a ring structure; and each b independently is 0 to 20. A particularly preferred nonionic surfactant of this tune has the formula

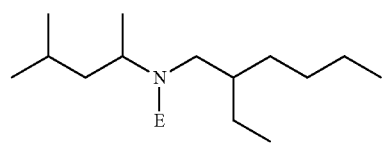

The surfactants of the present invention have the ability to reduce the surface tension of water. For instance, using illustrative embodiments of the surfactants at 0.1 weight percent concentration in water should provide solutions with an equilibrium surface tension of less than 50 mN/m. The dynamic surface tension of such illustrative embodiments would be less than 55 mN/m at bubble rate of 5 bubbles/second. Desirably, the contact angle on a Teflon film should be less than 75 degrees for more preferred embodiments.

The surfactants of the present invention can be used singly or in combination with other surfactants of the present invention or with other surfactants in a wide range of applications. The surfactants may be used in aqueous or nonaqueous compositions including solutions, dispersions, emulsions, latex compositions, gels, or the like. The surfactants would be particularly useful in any application in which low foaming, nonionic wetting agents are desired. For example, the surfactants would be useful in paint and other coating compositions, ink compositions, adhesive compositions, oil and gas recovery compositions, steam assisted gravity drainage compositions, chemical flooding compositions, cosmetics, foods, nutriceuticals, health care products, cleaning products, staining products, etching compositions, agrochemical compositions, or the like.

According to a preferred methodology for preparing nonionic surfactants of the present invention, a first step involves providing at least one adduct comprising at least one secondary amine moiety and at least two, branched hydrophobic moieties. In a second step, at least a portion of the secondary amine moieties of the adduct are N-functionalized under conditions effective to convert at least a portion of the secondary amine moieties to tertiary amine moieties having pendant, hydrophilic, N-ether functionality and thereby form the nonionic surfactant of the present invention described above.

As used herein, N-functionalized means that that the functionality is caused to be pendant from the nitrogen of the amine moiety, converting it from a secondary amine to a tertiary amine. N-ether means that the ether is pendant directly or indirectly from the resultant tertiary amine.

The adduct provided in the first step generally has the formula

wherein A is an n-valent moiety comprising one or more secondary amine moieties; each $R^1$ independently is as defined above such as a branched, hydrophobic moiety or is a member of a hydrophobic ring structure with another $R^1$; and n is 2 to 10, preferably 2 to 6. In illustrative embodiments, the adduct comprises a compound having a formula selected from the following or is a combination thereof:

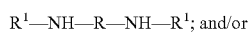

wherein each $R^1$ independently is as defined above such as a branched, hydrophobic moiety or a co-member of a hydrophobic ring structure with another $R^1$; R is a divalent linking moiety as defined above; $R^{15}$ is a p-valent moiety; and p is 3 to 10.

One representative class of adducts of the present invention has the formula

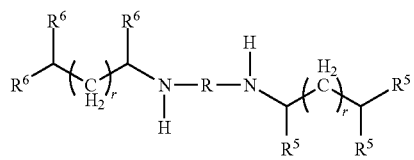

wherein R, $R^5$, and $R^6$ are independently as defined above. One preferred adduct according to this formula has the structure

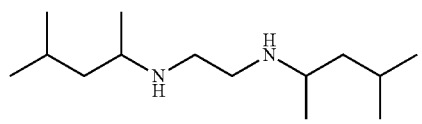 [SMILES: CC(C)CC(C)NCCNC(C)CC(C)C]

Another preferred adduct according to this formula has the structure

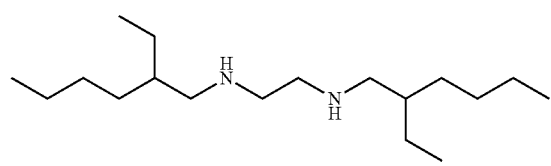 [SMILES: CCCCC(CC)CNCCNCC(CC)CCCC]

Another representative class of adducts of the present invention has the formula

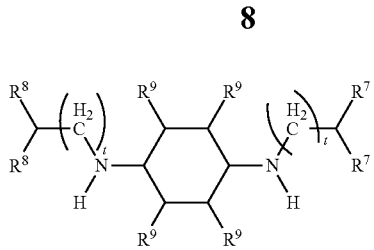

wherein each of $R^7$, $R^8$, and $R^9$ independently is as defined above. One preferred adduct according to this formula has the structure

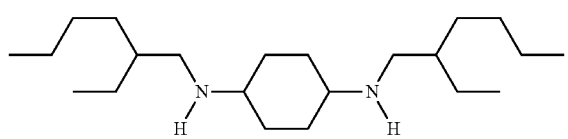 [SMILES: CCCCC(CC)CNC1CCC(NCC(CC)CCCC)CC1]

Another representative class of adducts of the present invention has the formula

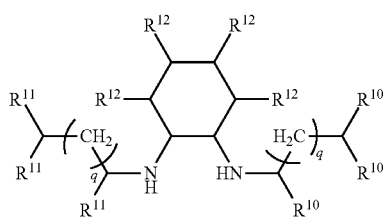

wherein each $R^{11}$, $R^{12}$, and $R^{13}$ independently is as defined above. One preferred adduct according to this formula has the structure

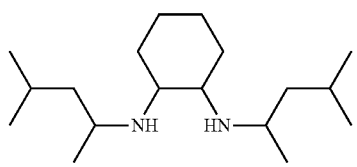 [SMILES: CC(C)CC(C)NC1CCCCC1NC(C)CC(C)C]

Another representative class of adducts of the present invention has the formula

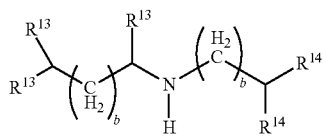

wherein each $R^{13}$ and each 14 independently is as defined above. One preferred adduct according to this formula has the structure

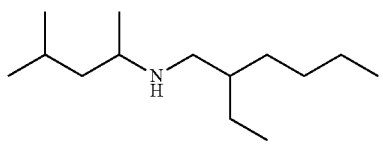

The adduct can be prepared by reacting ingredients comprising first and second compounds under conditions effective to form the adduct, wherein the first compound comprises one or more ketone and/or aldehyde moieties and the second compound comprises one or more primary amine moieties. Illustrative conditions for forming the adduct from such first and second reactant compounds include reductive amination conditions. Reductive amination techniques are further described in (1) "The Preparation of Amines by Reductive Alkylation", Emerson, W., Organic Reactions, Vol. 4, 174-255 (1948); (2) "Reductive Aminations of Carbonyl Compounds with Borohydride and Borane Reducing Agents", Baxter E. W.; Reitz, A. B., Organic Reactions, Vol 59, 1-714 (2002); (3) Abdel-Magid et al. Org. Process Res. Dev. 2006, 10, 971-1031; (4) Abdel-Magid et al. J. Org. Chem. 1996, 61, 3849-3862.

The hydrophobic, branched moieties may be sourced from either the first and/or second compounds. The first and/or second compounds can be symmetric or asymmetric. The first and/or second compounds can be linear, branched or cyclic; aliphatic or aromatic; and may be saturated or unsaturated. The first and/or second compounds preferably may include from 3 to 24 carbon atoms with the proviso that at least one of the first and second compounds provides a source of the branched hydrophobic moiety to be incorporated into the resultant adduct.

The first compound can include any one or more compounds that include one or more ketone and/or one or more aldehyde moieties. Exemplary aldehydes include 2-ethylhexanal, glyoxal, 2-ethylhex-2-enal, 2-propylhept-2-enal and 2-methylpent-2-enal, 2-propylheptanal, benzaldehyde, cinnamaldehyde, acetaldehyde; and combinations of these. Exemplary ketones include methyl isobutyl ketone, di-isobutyl ketone, cyclohexanone, 1,4-cyclohexanedione, 1,2-cyclohexanedione, 1,3-cyclohexanedione, acetone, methyl ethyl ketone, di-isopropyl ketone, 2,6,8-trimethylnonan-4-one, 2-pentanone, 2-hexanone, 2-heptanone, 2-octanone, and combinations of these.

In addition to the ketone and/or aldehyde moiety, the first compound may optionally include one or more other kinds of functionality that are compatible with the reductive amination and that would not unduly compromise the subsequent alkoxylation on the next reaction stage and/or unduly compromise performance of the resultant surfactant. Examples of such optional functionality include hydroxyl, alkenyl, alkynyl, secondary and tertiary amine, amide, ether, thioether and thiol moieties.

The second compound may include any one or more compounds including one or more primary amine moieties. Exemplary primary amines include one or more of 1,2-ethylene diamine, 1,3-propylene diamine, 1,2-cyclohexyldiamine, 1,3-cyclohexyldiamine, 1,4-cyclohexyldiamine, p-phenylenediamine, o-phenylenediamine, m-phenylenediamine, 2-ethylhexyl amine, 2-propylheptyl amine, 2,4,4-trimethylpentan-2-amine, isopropylamine, isobutylamine, isopentylamine and combinations thereof.

In addition to the primary amine moiety, the first compound may optionally include one or more other kinds of functionality that are compatible with the reductive amination and that would not unduly compromise the subsequent alkoxylation on the next reaction stage and/or unduly compromise performance of the resultant surfactant. Examples of such optional functionality include secondary and tertiary amine moieties, hydroxyl, alkenyl, alkynyl, amide, ether, cyano, nitro, thioether and thiol moieties.

Reductive amination typically takes place in the presence of one or more reducing agents. Any such agent(s) known to be useful for reductive amination may be used in the practice of the present invention. Exemplary reducing agents include borohydride systems such as sodium borohydride, sodium triacetoxyborohydride and sodium cyanoborohydride as well as hydrogenation catalysis systems such as palladium, platinum, rhodium, ruthenium and nickel-based catalyst systems under $H_2$ pressure.

According to a representative reaction scheme, the first compound and second compound are placed into a suitable reaction vessel in a suitable solvent in the presence of the reducing agent. The reaction may be carried out on a batch or continuous basis as desired. The stoichiometry may be selected so that the first compound is in excess so that the first compound end caps the second compound. In other modes of practice, the stoichiometry is selected so that the second compound end caps the first compound. In some instances, the stoichiometry may be substantially 1:1. In still other modes of practice, alternative stoichiometries may be practiced to achieve other reaction goals.

The reaction is allowed to progress at a suitable temperature for a suitable time period often under a protected atmosphere. By way of example, allowing the reaction to proceed at room temperature under a nitrogen atmosphere for 10 to 36 hours would be suitable.

After the reaction is complete, the reaction may be quenched, and the products may be extracted into an organic phase. A high purity product can then be recovered from the organic phase using any desired recovery techniques.

According to an alternative strategy, the adduct can be provided by using reductive amination techniques to form the adduct from one or more compounds that include at least one primary amine moiety and at least one aldehyde and/or ketone moiety. These compounds are multifunctional in the sense that they contain at least two different kinds of functionality, namely a primary amine and at least an aldehyde and/or ketone in the same compound. In other modes of practice, the adduct can be formed from reactants including at least one of the first and/or second compounds described above and at least one multifunctional reactant compound.

To prepare a nonionic surfactant of the present invention, one or more adducts provided in the first step are N-functionalized via a reaction strategy that adds respective hydrophilic moieties to one or more of the secondary amine moieties of the adduct(s). The moieties independently may be hydrophilic ether or polyether moieties containing, by way of example, 1 to 200 ether units, added independently to one or more of the secondary amines of the adduct(s). In more preferred embodiments, two or more of the secondary amines of the adduct(s) are N-functionalized with hydrophilic moieties. In some modes of practice, the degree of functionalization of the secondary amines is matched as closely as practical on average. For example, if two or more amines are functionalized by hydrophilic groups, it is desired that the average degree of functionality of a first first amine moiety is $X_1$, then it is desired that the average degree of functionality of the other functionalized amines is at least 50%, or even at least 70%, or even 100% of $X_1$.

By way of example, consider a surfactant embodiment containing two tertiary amines functionalized with —(CH₂CH₂O)— (ethylene oxide) groups. If the first amine moiety is functionalized with an average of 4 ethylene oxide groups, then it is desired that the other amine also is functionalized with 2 to 8, preferably 2.8 to 5.7, preferably 5 ethylene oxide groups.

According to one illustrative mode of practice, the secondary amine moieties of the adduct(s) are N-functionalized under suitable conditions to convert the secondary amine moieties to tertiary amine moieties having directly or indirectly pendant N-ether (or N-polyether) functionality. Representative conditions include reacting the adduct(s) with one or more epoxy functional compounds such as those including from 2 to 12 carbon atoms. Examples of such compounds include one or more of ethylene oxide, propylene oxide, butylene oxide, and combinations thereof.

The N-functionalization of the amines with these compounds to provide pendant ether or polyether chains is known in the art as alkoxylation. As known in the art, alkoxylation may involve alkoxylation with more than one type of resultant alkylene oxide. Thus, the alkylene oxide units may be the same or different. If different, the alkylene oxide units may be random or arranged in blocks.

An amine may be alkoxylated by any desired number of alkylene oxide units. In representative embodiments, at least one amine of an adduct, preferably at least two amines of each adduct is alkoxylated with 1 to 100, preferably 1 to 20, more preferably 1 to 6 alkylene oxide units.

The alkoxylation reaction desirably occurs in the presence of a catalyst, optionally in a suitable solvent. The catalyst may be any catalyst or combination of catalysts known to be useful for carrying out alkoxylation reactions. Representative examples include KOH, NaOH, KH, NaH and double metal cyanide (DMC) catalysts. Suitable solvents also are widely known and any may be used. Examples include dimethoxyethane and toluene.

According to a representative alkoxylation methodology, an adduct, solvent and catalyst are loaded into a suitable reaction vessel. An exemplary reaction vessel is pressurized to facilitate the reaction. The reaction may occur on a batch or continuous basis. The desired epoxy functional reactant may then be supplied at the desired stoichiometric excess to achieve the desired functionalization. For instance, 4 equivalents of epoxide can be supplied per equivalent of amine to achieve an average functionalization of 4 alkylene oxide units per amine. The reaction is allowed to proceed at elevated pressure and temperature until complete. The reaction product can then be recovered using conventional recovery techniques.

The present invention will now be further described with reference to the following illustrative examples.

Example 1

Methyl isobutyl ketone (MIBK) (6.050 g, 60.403 mmol, 1 equiv.), ethylene diamine (1.815 g, 30.202 mmol, 0.5 equiv.) and sodium triacetoxyborohydride (15.362 g, 72.484 mmol, 1.2 equiv.) in about 175 mL CH₂Cl₂ were weighed into a 500 mL three-necked flask. The mixture was stirred at room temperature under a nitrogen atmosphere. The reaction was stopped after a total of 20 h. The mixture was quenched with saturated aqueous NaHCO₃ and the product extracted into ethyl acetate. The combined organic fraction was dried over sodium sulfate, filtered and evaporated using a rotovap to yield 3.774 g of desired product. The product, N,N'-bis(4-methylpentan-2-yl)ethane-1,2-diamine, had high purity as determined by gas chromatography and NMR. This adduct has the following structure:

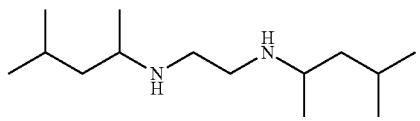 [SMILES: CC(C)CC(C)NCCNC(C)CC(C)C]

Example 2A

N,N'-bis(4-methylpentan-2-yl)ethane-1,2-diamine (1.00 g, 4.38 mmol, 1 equiv.), 1,2-dimethoxyethane (1 mL), KH (3-5 mg, 0.3-0.5 wt. %) were loaded into a glass PPR vial (insert). Alkoxylation was carried out in a Symyx PPR® (Parallel Pressure Reactor) setup containing 48 reactors. Ethylene oxide (EO) was delivered via an Isco syringe pump equipped with a robotically-controlled needle and compressed gas microvalve connected to the PPR, such that 4 equivalents of EO were added per molecule of diamine initiator on average. A glass insert along with a removable PEEK stir paddle for the cell were dried in a vacuum oven at 125° C. overnight. The insert with the diamine, 1,2-dimethoxyethane and KH was loaded into each PPR well, heated to 130° C., and pressurized with nitrogen to 50 psi. EO was introduced at 130° C. and the reaction was stirred for 12 h at that temperature. After cooling and venting, the insert was placed in a Savant SC250EXP SpeedVac® Concentrator for 1 h at 80° C. and 0.01 Torr. The resulting viscous surfactant was tested for its properties without additional purification. The identity of the surfactant was confirmed by NMR spectroscopy. The ethoxylated surfactant of this Example 2A has the following structure where the sum of $x+y=4$ is an average:

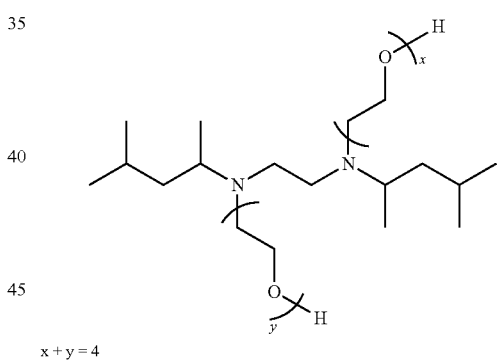

$x + y = 4$

Example 2B

The procedure of Example 2A is repeated to prepare a surfactant, except a catalyst is not used.

Example 2C

The procedure of Example 2A is repeated to prepare a surfactant, except a solvent is not used.

Example 3

Basic surfactant properties of the surfactant from EXAMPLE 2A were characterized. The equilibrium surface tension of a 0.1 wt % aqueous solution is reduced to 29 mN/m, and the dynamic surface tension at 5 bubbles/second is 37 mN/m. The contact angle on a TEFLON film is reduced to 70 degrees, and the contact angle on polyethylene is reduced to 46 degrees. As summarized in table 1 below, the ethoxylated diamine surfactant from EXAMPLE 2A exhibits better properties than the non-ethoxylated precursor prepared in Example 1.

Basic surfactant properties also were characterized on the non-ethoxylated precursor from EXAMPLE 1. The equilibrium surface tension of a 0.1 wt % aqueous solution is reduced to 36 mN/m, the dynamic surface tension of a 0.1 wt % aqueous solution at 5 bubbles/second is 37 mN/m, the contact angle on a Teflon film is 90 degrees, and the contact angle on polyethylene is 62 degrees. Data is summarized in the following Table 1.

TABLE 1

Comparison of basic surfactant properties of non-ethoxylated diamine-based molecule with those of the corresponding ethoxylated version.

|  | Example 1 Precursor aqueous solution (0.1 wt %) | EXAMPLE 2 aqueous solution (0.1 wt %) |
|---|---|---|
| Equilibrium surface tension, mN/m | 36 | 29 |
| Dynamic Surface Tension at 5 bbl/sec, mN/m | 37 | 40 |
| Contact angle on polyethylene, degree | 62 | 46 |
| Contact angle on Teflon, degree | 90 | 70 |

Example 4

MIBK (6.843 g, 59.93 mmol, 1 equiv.), 2-ethylhexyl amine (7.745 g, 59.93 mmol, 1 equiv.) and sodium triacetoxyborohydride (17.780 g, 84.37 mmol, 1.4 equiv.) were weighed into a 500 mL three-necked flask and suspended in about 175 mL CH$_2$Cl$_2$. The mixture was stirred at room temperature under a nitrogen atmosphere for 64 h after which time the reaction was complete. The mixture was then quenched with saturated aqueous NaHCO$_3$ and the product extracted into ethyl acetate. The combined organic fraction was dried over sodium sulfate for 5 h. After filtration, the solution was rotovaped to give 10.775 g of the desired product as a slightly yellow liquid. GC analysis of the isolated product showed purity of 98%.

Example 5

1,4-Cyclohexanedione (3.037 g, 27.08 mmol, 1 equiv.), 2-ethylhexyl amine (7.000 g, 54.16 mmol, 2 equiv.) and sodium triacetoxyborohydride (13.775 g, 65.00 mmol, 1.2 equiv.) were weighed into a 500 mL three-necked flask and suspended in about 160 mL CH$_2$Cl$_2$. The mixture was stirred at room temperature under a nitrogen atmosphere for 22 h after which time the reaction was complete. The mixture was then quenched with saturated aqueous NaHCO$_3$ and the product extracted into ethyl acetate. The combined organic fraction was dried over magnesium sulfate for 5 h. After filtration, the solution was rotovaped to give 7.232 g of the desired product as a dark brown liquid. GC analysis of the isolated product showed purity of 98%.

Example 6

MIBK (6.130 g, 61.202 mmol, 1 equiv.), 1,2-diaminocyclohexane (3.494 g, 30.601 mmol, 0.5 equiv.) and sodium triacetoxyborohydride (15.565 g, 73.442 mmol, 1.2 equiv.) were weighed into a 500 mL three-necked flask and suspended in about 175 mL CH$_2$Cl$_2$. The mixture was stirred at room temperature under a nitrogen atmosphere for 19 h after which time the reaction was complete. The mixture was then quenched with saturated aqueous NaHCO$_3$ and the product extracted into ethyl acetate. The combined organic fraction was dried over magnesium sulfate for 5 h. After filtration, the solution was rotovaped to give 8.490 g of the desired product as an off-white paste. GC analysis of the isolated product showed purity of 94%. $^1$H NMR (CD$_3$OD, 500 MHz, RT): δ=0.84-0.96 (m, 12H), 1.03-1.78 (m, 14H), 1.12-1.20 (m, 6H), 2.10-2.18 (m, 1H), 2.43-2.58 (m, 1H), 2.88-3.12 (m, 2H). The following shows the structures of precursors from EXAMPLES 4-6, respectively.

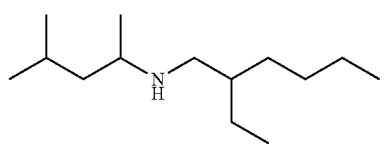

EXAMPLE 4

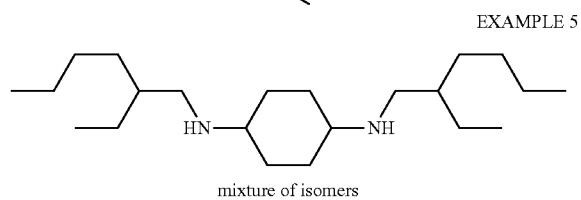

EXAMPLE 5 mixture of isomers

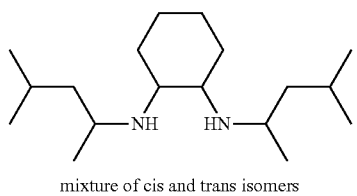

EXAMPLE 6 mixture of cis and trans isomers

Examples 7-9

The corresponding amine or diamines from Examples 4-6, respectively, (1.00 g), 1,2-dimethoxyethane (1 mL) (the reaction may be conducted without solvent), and KH (3-5 mg, 0.3-0.5 wt. %) (the reaction may also be carried out without any catalyst) were loaded into a glass PPR vial (insert). Alkoxylation was carried out in a Symyx PPR® (Parallel Pressure Reactor) setup containing 48 reactors. Ethylene oxide (EO) was delivered via an Isco syringe pump equipped with a robotically-controlled needle and compressed gas microvalve connected to the PPR, such that required equivalents of EO were added per molecule of amine precursor. A glass insert along with a removable PEEK stir paddle for the cell were dried in a vacuum oven at 125° C. overnight. The insert with the amine, 1,2-dimethoxyethane and KH was loaded into each PPR well, heated to 130° C., and pressurized with nitrogen to 50 psi. EO was introduced at 130° C. and the reaction was stirred for 12 h at that temperature. After cooling and venting, the insert was placed in a Savant SC250EXP SpeedVac® Concentrator for 1 h at 80° C. and 0.01 Torr. The resulting viscous surfactants are identified as Examples 7-9, respectively, and were tested for their properties without additional purification. The identity of the surfactants was confirmed by NMR spectroscopy.

Examples 10

Basic surfactant properties were characterized on the surfactants from EXAMPLES 7-9, where the ethylene oxide (EO) content is 4, 3.5 and 8 equivalents, respectively. Table 2 summarizes the results obtained.

TABLE 2

Comparison of basic surfactant properties of non-ethoxylated amine-based molecules from EXAMPLES 4-6 with those of the corresponding ethoxylated versions from EXAMPLES 7-9.

|  | EXAMPLE 7 | COMPARATIVE EXAMPLE 2 | EXAMPLE 8 | COMPARATIVE EXAMPLE 3 | EXAMPLE 9 | COMPARTIVE EXAMPLE 4 |
|---|---|---|---|---|---|---|
| Corresponding Surfactant | EXAMPLE 7 | EXAMPLE 4 | EXAMPLE 8 | EXAMPLE 5 | EXAMPLE 9 | EXAMPLE 6 |
| Equilibrium surface tension, mN/m | 39 | 60 | 33 | 42 | 46 | 65 |
| Dynamic Surface Tension at 5 bbl/sec, mN/m | 54 | 70 | 50 | 71 | 37 | 62 |
| Contact angle on polyethylene, degree | 64 | 81 | 58 | 75 | 62 | 86 |
| Contact angle on Teflon, degree | 75 | 91 | 70 | 101 | 88 | 102 |

Note:
All tests done on aqueous solutions (0.1 wt %).

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A nonionic surfactant with the following formula

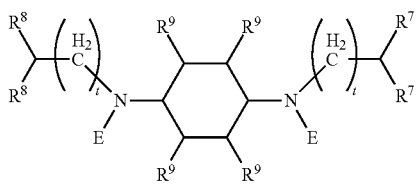

wherein each $R^7$ and each $R^8$ independently is a monovalent moiety comprising 1 to 20 carbon atoms; each $R^9$ independently is H, a monovalent moiety comprising 1 to 20 carbon atoms; and each t independently is 1 to 20; each E independently is H or an N-functional, monovalent moiety of the formula

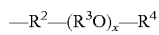

with the proviso that at least one E is not H, wherein each $R^2$ independently is a single bond or a divalent linking group; each $R^3$ is independently an alkylene moiety containing from 1 to 5 carbon atoms; each x independently is 1 to 100; and each $R^4$ independently is H or a monovalent moiety comprising from 1 to 8 carbon atoms.

2. A nonionic surfactant with the following formula

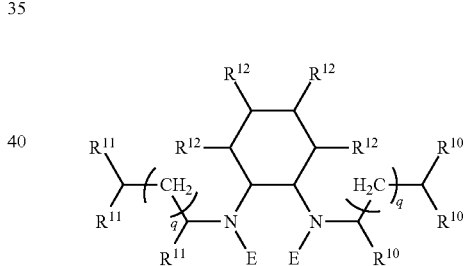

wherein each $R^{10}$ and each $R^{11}$ independently is a monovalent moiety comprising 1 to 20 carbon atoms; each $R^{12}$ independently is H, a monovalent moiety comprising 1 to 20 carbon atoms; and each q independently is 1 to 20; each E independently is H or an N-functional, monovalent moiety of the formula

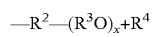

with the proviso that at least one E is not H, wherein each $R^2$ independently is a single bond or a divalent linking group; each $R^3$ is independently an alkylene moiety containing from 1 to 5 carbon atoms; each x independently is 1 to 100; and each $R^4$ independently is H or a monovalent moiety comprising from 1 to 8 carbon atoms.

3. A paint, an ink, an adhesive, a coating, or an oil and gas recovery composition comprising the nonionic surfactant of claim 1 or claim 2.

* * * * *